United States Patent [19]

Jones

[11] Patent Number: 4,834,098

[45] Date of Patent: May 30, 1989

[54] SUTURING NEEDLE AND ANCHOR

[75] Inventor: J. Paul Jones, Chester Springs, Pa.

[73] Assignee: PRD Corporation, Exton, Pa.

[21] Appl. No.: 162,260

[22] Filed: Feb. 29, 1988

Related U.S. Application Data

[62] Division of Ser. No. 916,896, Oct. 8, 1986, Pat. No. 4,732,151.

[51] Int. Cl.⁴ .............................................. A61B 17/06
[52] U.S. Cl. ...................................... 128/339; 128/340
[58] Field of Search ................... 128/335, 334 C, 337, 128/340, 334 R, 335.5, 339; 24/150 R, 150 FP, 150 P

[56] References Cited

U.S. PATENT DOCUMENTS

| | | | |
|---|---|---|---|
| 2,266,432 | 12/1941 | Morin et al. | 24/150 P |
| 2,361,860 | 10/1944 | Mason | 24/150 B |
| 3,570,497 | 3/1971 | Lemole | 128/339 |
| 3,851,359 | 12/1974 | Wilson | 24/150 R |

FOREIGN PATENT DOCUMENTS

| | | | |
|---|---|---|---|
| 17468 | of 1909 | United Kingdom | 24/150 R |
| 793940 | 4/1958 | United Kingdom | 24/150 P |

Primary Examiner—Richard C. Pinkham
Assistant Examiner—Gary Jackson

[57] ABSTRACT

A suturing needle in combination with an anchor. The anchor is molded from medical grade plastic. The needle is made of surgical grade steel and is formed in an arcuate shape. One end of the needle has a point. The opposite end has an off-set section which is insert-molded with the anchor. The off-set section maintains the anchor and needle together. The body is formed with a pair of square cavities whose axes are coaxial. The cavities receive square projections on a manipulating tool.

5 Claims, 5 Drawing Sheets

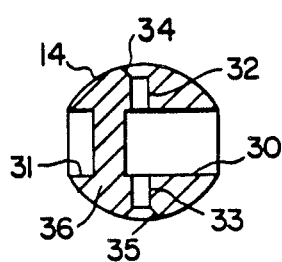
FIG. 9
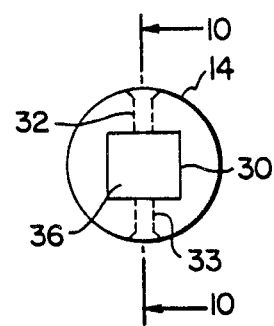
FIG. 10
FIG. 11
FIG. 12
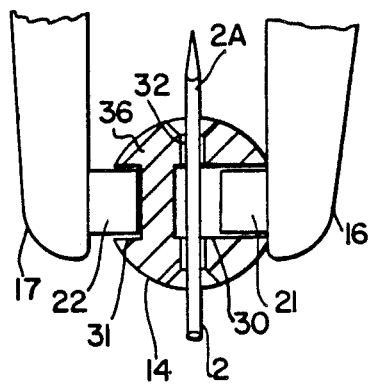
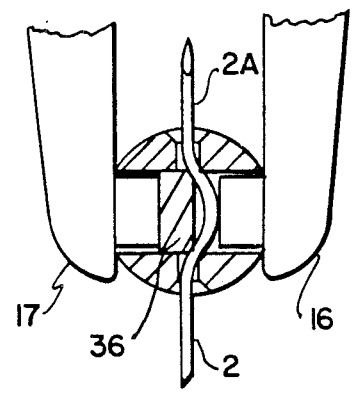

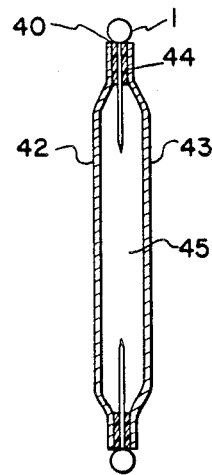
FIG. 13
FIG. 14
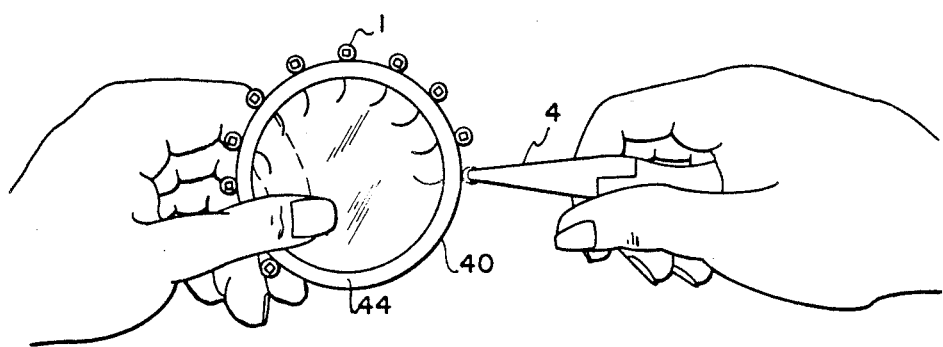

SUTURING NEEDLE AND ANCHOR

This application is a division of my copending application Ser. No. 916,896 filed Oct. 8, 1986 and now U.S. Pat. No. 4,732,151. The claims are directed to the combination of a suturing needle and an anchor.

This invention relates to an improved needle for suturing surface cuts or wounds which overcomes most of the problems that are inherent in the presently used needles while at the same time reducing the number of steps that are in normal suturing.

The "curved sewing needle" and stitching thread have long been the standard components of suturing systems. The enlarged eye on one end of the needle, combined with double thickness thread, causes considerable trauma to the flesh adjacent to the wound and can introduce micro particles that cause the wound to become infected and also can inhibit healing.

There are new very thin needles with monofilament "thread" staked into a small hole in the back end of the needle which greatly reduce the penetration trauma. However, the thin needle and stitching material makes the tie back problem even worse.

The problem with any thin thread stitch which is tied back over the wound is the extraordinary pressure (pounds per square inch) on the very thin thread and the adjacent tissue necessary to hold the wound together.

Some prior art shows individual anchors tied to the thread ends at both sides of the wound. This approaches the direct answer to the "flesh cutting" problem by: (1) spreading the holding force over a wide area; (2) allowing the wound to remain uncovered for cleaning and dressing; and (3) keeping any stitching out of the wound. However, making the knot at just the right tension points, under the normally bloody conditions, can be too difficult to be practical.

Developments toward a quickly installed suture include the skin clamp which is much like a staple. Although quick, this method departs from low trauma and low scarring principles. Furthermore, the clamps are in intimate contact with the wound which is a negative factor.

There have been other steps toward the ideal suture in micro-surgery particularly for operations that are made on the eye. Extremely thin needles are used to make the micro-stitches and the thin metal needles remain as the stitches. Fortunately, there is very little force on the stitches until they are removed.

The invention contemplates providing equipment for general suturing. The suture is a very thin, preferably surgical grade steel needle on one end of which is firmly secured a small anchor which is adapted to be grasped by a special tool to manipulate the needle for insertion. When the needle is fully inserted, the anchor engages the body in one side of the cut or wound and the other end of the needle protrudes out of the body. The same special tool is used to put a second, crimped-on anchor on the protruding needle end while pressing the wound to close the same, the tool, when the cut is closed, is operated to crimp the second anchor in place.

Advantageously, the small anchors distribute holding pressure over a wide area with vector forces directed at an angle to hold the flesh together for the depth of the wound. Moreover, since the small anchors are located along both sides of the wound, they act at spacers to keep ordinary bandages from coming in contact with the wound.

The invention will be described below in connection with the following drawings wherein:

FIG. 9 is a sectional view of the crimp-on anchor which is secured or crimped to the end of the needle which protrudes after the needle has been inserted;

FIG. 10 is a side view looking toward the left in FIG. 9 without the anchor being sectioned;

FIG. 11 is an enlarged view partially in section of the crimp-on anchor and tool in the initial stage of the crimping operation;

FIG. 12 is a view like FIG. 6 and showing the tool in the first stage of the crimping operation;

FIG. 13 is a sectional elevational view of a dispenser for a plurality of needle and anchor assemblies;

FIG. 14 is a view showing how the needle and anchor assembly is removed from the dispenser;

I will first describe the new method of suturing, and then describe the novel tools for practicing this method, and lastly, the packaging arrangement.

The method will be described in connection with FIGS. 1–4.

Figure 1:
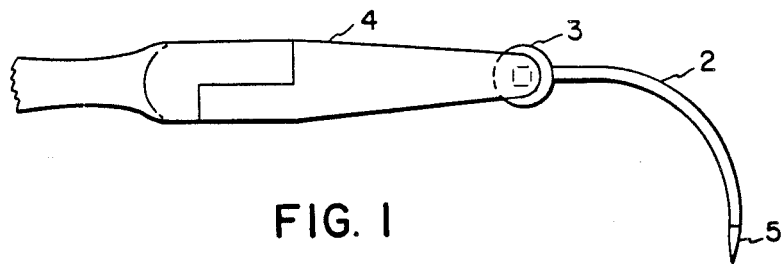
FIG. 1 is a side view showing the tool of the invention holding the anchor of the needle and anchor assembly for inserting the needle in the patient's body.

Referring to FIG. 1, the needle and anchor assembly 1 includes the thin, arcuately-shaped needle 2 and the anchor 3. The anchor 3 is gripped by the manipulating tool 4. The needle has a sharp tip 5.

Figure 2:
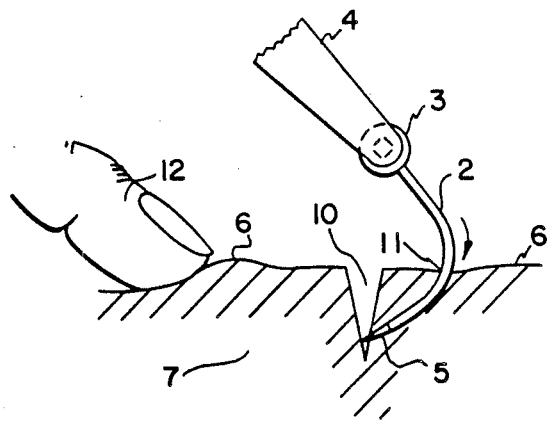
FIG. 2 is a diagramatic view showing the initial stage of the needle-inserting operation.
Figure 3:
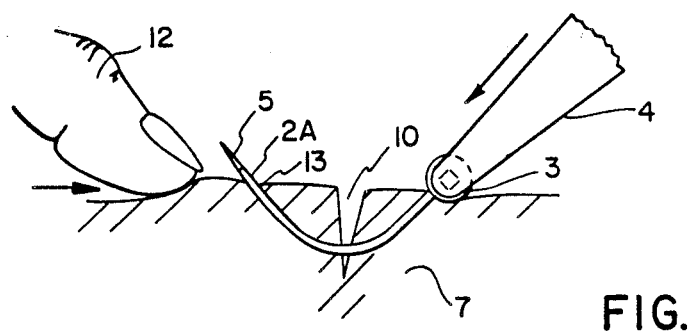
FIG. 3 is a diagramatic view showing the position of the needle and its anchor when fully inserted and the pointed end of the needle protruding from the body.
Figure 4:
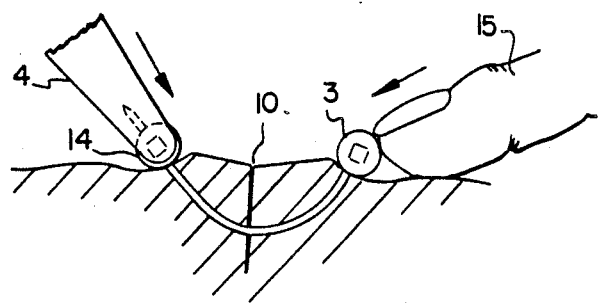
FIG. 4 is a diagramatic view showing the wound closing and crimp-on anchoring operation.

In FIG. 2 the needle and anchor assembly 1 is shown held by the tool 4 above the body surface 6 with the needle 2 penetrating into the flesh 7 on one side of the open cut or wound 10.

Needle penetration is effected by moving the tool so that the needle first engages the body surface 6 at the entry point 11 with the assembly oriented to effect motion through the flesh in an arcuate path. At this time the finger 12 is engaged with the body surface 6 and exerts a force down and toward the cut 10. The tool is moved in an arc so that the needle penetrates and follows an arcuate path through the cut and through the flesh on the opposite side of the cut upwardly to exit at the exit point 13.

The acruate penetrating motion continues until the tool has moved the anchor 3 against the body surface at the entry point 11 and the tip 5 on portion 2a of the needle protrudes beyond the exit point 13 and above the surface 6. Note at this stage that the cut 10 is still open.

Next, a second anchor 14 is gripped by the tool 4 and slipped over the tip 5 and protruding section 2a. One finger 15 of one hand engages the anchor 3 and moves to exert a force on the anchor downwardly and toward the cut 10. At the same time, the tool 4 is moved toward the cut 10. The forces on the anchors 3 and 14 move the flesh on opposite sides of the cut toward one another which causes the cut to close not only at the top but at the deepest points of separation. The force exerted on the anchor 14 moves the same further down on the needle.

When the cut is closed as above described, the tool is squeezed to securely crimp the anchor 14 on the needle. The tool 4 is then removed and the sharp point 5 of the needle is snipped off. Normally, the latter operation will be done after all sutures are set in place.

It will be evident that the above method eliminates the conventional tie-back problem and cuts down the number of steps necessary to close a wound. The cut is held together not by fine threads exerting pressure on the flesh where the thread exits, but by anchors which bear on the surface and act over a relatively large surface.

After the wound is healed, the suture is removed by snipping the needle under one of the anchors with a pair of diagonals. The remaining anchor and needle may then be easily slipped out without discomfort to the patient.

I will now explain the preferred structure of the tool 4, the needle 2, the anchor 3 of assembly 1, and the anchor 14.

Figure 5:
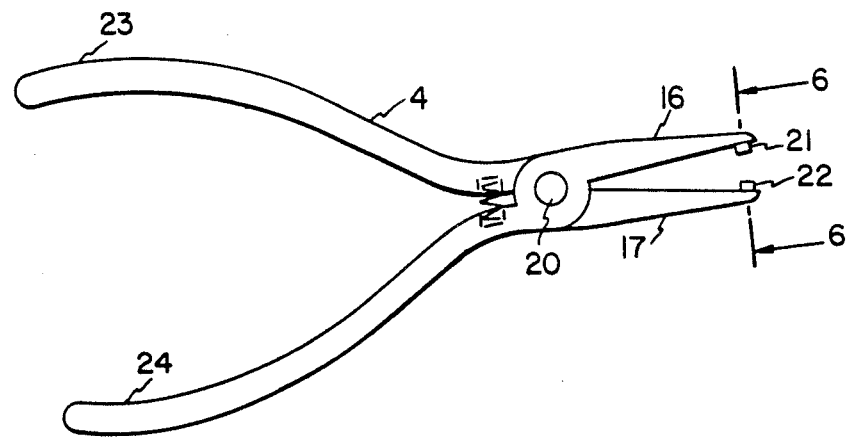
FIG. 5 is a side view of the special tool of the invention.
Figure 6:
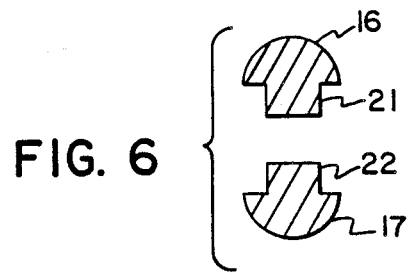
FIG. 6 is a view taken along the lines 6—6 of FIG. 5.

Referring to FIGS. 5 and 6, the tool 4 has a pair of arms 16 and 17 connected together by pivot means 20 which provide for the arms to relatively rotate in parallel planes. On one side of the pivot 20 each arm carries an opposing projection as indicated at 21 and 22. The projection faces in a clockwise direction and the projection 22 faces in the counterclockwise direction. The arms 16 and 17 mount the projections so that they rotate in a common plane so that as engaged they are aligned with one another. The projections 21 and 22 move together when the arms 23 and 24 are squeezed together by the operator.

As seen in FIG. 6a the projection 21 in cross section is square and uniform over the length of the projection, projection 22 has an identical cross section. The corresponding sides of the projections 21, 22 are co-planar. The projections also have the same length.

On the opposite side of the pivot 20, the grasping arms are configured as indicated at 23 and 24 to provide gripping means by which the tool can be held in either the left or right hand.

The needle and the needle and anchor assembly 1 will now be described.

Figure 7:
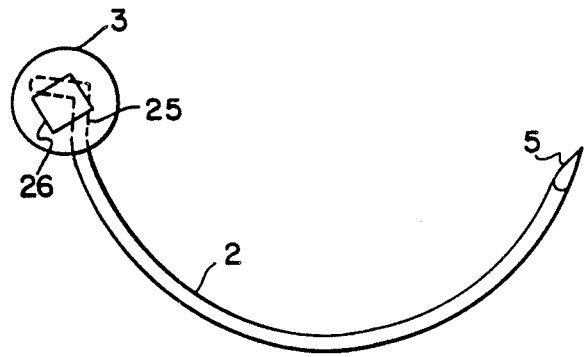
FIG. 7 is a side view of the needle and anchor assembly.
Figure 8:
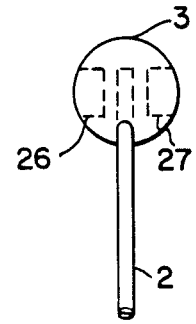
FIG. 8 is an end view of the anchor and part of the needle in FIG. 7.
Figure 15:
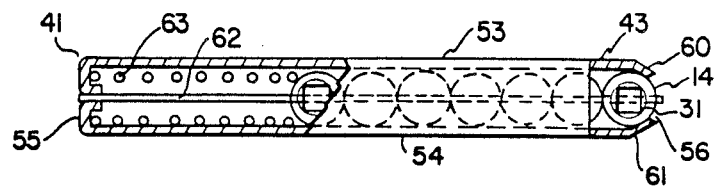
FIG. 15 is an elevational view partially in section showing a dispenser for the crimp-on anchors.
Figure 16:
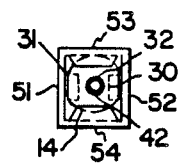
FIG. 16 is an end view looking toward the left in FIG. 15.
Figure 17:
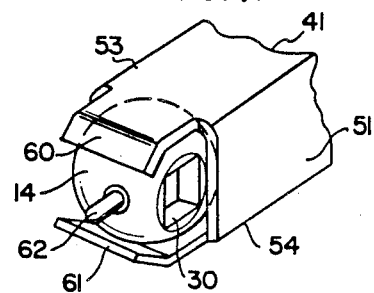
FIG. 17 is a perspective view of the end of the dispenser of FIG. 15.
Figure 18:
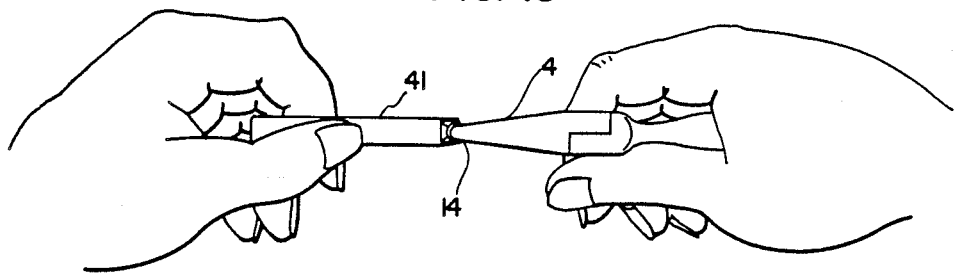
FIG. 18 is a view showing how the crimp-on anchors are removed from the dispenser of FIG. 16.

Referring to the needle 2 in FIGS. 7 and 8, it is pointed out that thin surgical needles are known per se. Such needles are conventionally made from surgical grade stainless steel and have sharp, three-sided pyramid-like points. The needle suture of this invention has the foregoing characteristic and importantly is very thin being in the range of 0.010 inches in diameter.

The anchor 3 of the invention is preferably spherical or ball-shaped and is molded from medical grade plastic such as Delrin or Nylon. Typically, the ball is 0.10 inches in diameter.

The needle 2 and the anchor 3 are combined together during insert molding. The needle 2 has an off-set section 25 which is surrounded by the plastic anchor.

For purposes of being gripped by the tool 4, the ball 3 is formed with cavities 26 and 27 which extend from the surface of the ball into the anchor. The cavities are square in cross-section, have the same dimensions, and their axes are coaxial and the corresponding sides of the cavities are co-planar.

The purpose of the cavities 26 and 27 is to receive the projections 21 and 22 on the tool 4 and hold the anchor 3 firm on the tool. The lateral dimensions of the sides of the cavities are slightly greater than the corresponding lateral sides of the projection so as to permit the projections to enter the cavities and be released therefrom. The outer edge of the projection and the outer edge of the cavities may be chamfered to facilitate entry of the projection.

The structure of the anchor 14 will be described in connection with FIGS. 9 and 10.

The anchor 14, like the anchor 3, is preferably spherical or ball-shaped and is molded from medical grade plastic, and is typically 0.10 inches in diameter.

The anchor 14 has first and second cavities 30 and 31 extending into the anchor from the surface. The cavities 30 and 31 are square in cross-section, they have the same dimensions, their axes are coaxial, and the corresponding sides are co-planar. The axes of the cavities 30 and 31 lie along a diameter of the sphere.

The cavities 30 and 31 are adapted to receive the projections 21 and 22 of the tool. Except for depth, the dimensions of cavities 30 and 31 are identical to the dimensions of cavities 26 and 27 of anchor 3 so that the tool 4 can be employed for both anchors. The outer edges of the cavities 30 and 31 can be chamfered.

The anchor 14 has third and fourth aligned apertures 32 and 33 each extending inwardly from the surface. The inner ends of both apertures 32 and 33 are open to the cavity 30. The axes of the apertures 32 and 33 are co-axial and lie along a diameter of the sphere and intersect the axes of the cavities 30 and 31. The outer ends of the apertures 32 and 33 are chamfered at 34 and 35. As will be noted shortly, the purposes of apertures 32 and 33 is to receive the protruding end 2a of the needle.

With reference to FIG. 9, it will be observed that the cavity 30 extends inwardly to a greater depth than cavity 31. The affect of this is to create the barrier 36 which is offset from the apertures 32 and 33. This barrier is used to secure the anchor 14 and needle 2 together as will be explained.

As shown in FIG. 11 the cavities 30 and 31 are aligned to receive the corresponding projections 21 and 22 on the tool 4. On the right side the tip of the arm 16 has engaged the anchor 14 and the projection 21 is fully into its cavity 30 with space to spare. On the left side, the opposing projection 22 has bottomed against the barrier 36. When pressure is applied to the tool handles 23 and 24 the sharp edged projection 22 acts as a punch, which shears the barrier 36 and effectively changes it into a movable "plug".

With continuation of the squeezing motion the "plug" will deform the needle tip 2a into the cavity 30 in front of the tool projection 21 until the tip of the arm 17 bottoms against the anchor 14. The final position of all parts, after the crimping action, is shown in FIG. 12. The tool projections 21, 22 may then be removed and a pair of "diagonal" cutters used to nip off the remaining tip 2a of the needle 2.

Under the conditions that typically exist when sutures are being administered, speed and efficiency are of great importance. The need for special skills and specialized training is also something that should be minimized because of the trend toward using paramedical persons to do what was reserved for the doctors in the past. With the present method of suturing, the instant availability of the needle and anchor assemblies and the crimp-on anchors is a necessity. Thus, the invention contemplates a packaging technique by which both the needle and anchor assemblies and the crimp-on anchors are disposed in sterile condition in hand-held dispensers and can be quickly taken out in ready condition for use by means of the tool 4. Both the needle and anchor assemblies and the crimp-on anchors are quickly removed from the dispensers without the need to touch either the needle or the anchor and thereby maintain the sterile condition.

FIG. 13 shows the disc-like dispenser 40 for the needle and anchor assembly 1 and FIG. 14 shows the way the tool 4 is used to extract the assemblies. FIGS. 15 through 18 respectively show the dispenser 41 for the crimp-on anchors 14 and the way the tool 4 is used to extract an anchor.

In FIG. 13, the disc-like dispenser 40 includes a pair of circular covers 42 and 43 made of transparent plastic material and extending generally parallel to one another. The outer edges of each cover extend inwardly and are separated by a ring of elastomer material 44 which is welded to the covers 42 and 43. This forms a sealed chamber 45.

The outer peripheral edges of the covers 42 and 43 and the ring 44 are all aligned so that the outer edge of the package is relatively smooth.

The individual needle and anchor assemblies are set up by causing the needle to pierce the elastomer material so that it extends into the chamber 45 with the anchor firm against the outer edge of ring 44. As noted in FIG. 14, several assemblies are set up around the outer edge of the dispenser. After loading the assemblies, the composite is radiation sterilized.

By holding the package 40 in one hand and the tool 4 in the other hand the projections 21 and 22 are engaged with the cavities 30 and 31 and the tool moved outwardly and arcuately to pull out the assembly. The assembly is now ready to be used as described in connection with FIGS. 1-4. It will be seen, therefore, that individual assemblies can be removed without the necessity of touching with the hands and in ready conditions for suturing.

Referring to FIGS. 15-18, the dispenser 41 comprises a hollow rectangular body 50 having sides 51, 52, and top and bottom 53 and 54. The end 55 is closed and the end 56 is open. Extending out from the top 53 and bottom 54 are inwardly curving flexible flaps 60 and 61. Inside of the body 50 is a rod 62 which is fixed to the end 55 and extends outwardly to the end 56 between flaps 60 and 61. On the rod is a plurality of crimp-on anchors 14 the outermost anchor 14 being disposed between the flexible flaps 60 and 61. A compression spring 63 bearing on the end 55 and the innermost anchor pushes the anchors outwardly so that outermost anchor is between flaps 60 and 61. The flaps 60 and 61 grip the outermost anchor such that the same will not pop out by the pressure of spring 63.

The anchors are held against rotation in the body 50 as explained following.

In the molding of the cavities 30 and 31, part of the full width of the sphere is eliminated so that the outer edges of cavities 30 and 31 respectively lie in parallel planes. The same condition pertains to the outer edges of the apertures 32 and 33. The sides 51 and 52 of the body are flat and the inside dimensions of the body are chosen so that the planar outer edges of cavities 30 and 31 slidably engage the sides 51 and 52. It will be apparent, therefore, that there are multiple engagements between planar edges on the anchor and flat, inner surfaces on the body and that this engagement prevents rotation of the anchors in a direction clockwise or counterclockwise as viewed in FIG. 16. The rod 62 in the apertures 32 and 33 prevents rotation of the anchors in a direction clockwise or counter-clockwise as viewed in FIG. 15.

An anchor will not fit into the body 50 and freely slide along the rod 52 unless it is oriented so that the planar areas on the anchor are aligned for engagement with the sides 51 and 52. This is done by making the space between the sides 51 and 52 the same as the distance between the planar edges of the anchor. Thus, all the anchors will have the same orientation in the dispenser.

Anchors are placed in the body 50 over the rod 55 with the corresponding cavities and apertures facing in the same direction; i.e. with the outer edge of the cavity 30 engaging side 52 and the outer edge of cavity 31 engaging the side 51. Thus, as an anchor is removed from its position between the flaps 60 and 61, the next anchor will appear with exactly Each anchor is removed as noted in FIG. 18; i.e. the dispenser 41 is held in one hand while the tool in the other hand is brought up to the anchor and the projections 21 and 22 are squeezed into the cavities 30 and 31 and thereafter the anchor pulled away.

After the anchors 14 are packaged in the dispenser as above described, the filled dispenser is sealed in a suitable container which is then radiated for purposes of sterilization.

Normally, body 50 of the dispenser is molded using a thermoplastic resin with the material comprising the flaps 61 and 72 in flat condition. After the anchors 14 are inserted, a hot die is employed to engage the flap material and cause the same to form into the shape shown. Also the resin is preferably clear so that the number of anchors in the dispenser can be observed.

I claim:

1. A needle in combination with an anchor, the combination being for use in suturing and comprising:
    a body molded from medical grade plastic;
    a needle made of surgical grade steel and formed in an arcuate shape, one end of the needle being formed with a point and the opposite end being embedded in said body; and
    a pair of spaced apart cavity means each having at least one planar surface and respectively extending into the body from the surface thereof for use in being engaged by a corresponding planar surface on a manipulating tool.

2. The combination of claim 1 wherein each cavity of said pair is square in cross section.

3. A needle in combination with an anchor, the combination being for use in suturing and comprising:
    a body molded from medical grade plastic; a needle made of surgical grade steel and formed in an arcuate shape, one end of the needle being formed with a point and the opposite end having at least one off-set section which is embedded in said body having been insert molded therewith, the off-set section maintaining the body and needle together; and the body being formed with first and second cavities each extending into the body from the surface thereof and being disposed on opposite sides of the body with the axis of the cavities being coaxial.

4. The anchor of claim 3 wherein said first and second cavities, in cross section, have a shape which includes at least one planar section.

5. The combination of claim 3 wherein said first and second cavities each are square in cross section.

* * * * *